United States Patent
Koch et al.

(10) Patent No.: US 10,064,589 B2
(45) Date of Patent: Sep. 4, 2018

(54) METHOD, APPARATUS, AND ARTICLE FOR PET ATTENUATION CORRECTION UTILIZING MRI

(71) Applicants: Kevin Matthew Koch, Milwaukee, WI (US); Gaspar Delso, Schlieren (CH)

(72) Inventors: Kevin Matthew Koch, Milwaukee, WI (US); Gaspar Delso, Schlieren (CH)

(73) Assignee: General Electric Company, Schenectady, NY (US)

( * ) Notice: Subject to any disclaimer, the term of this patent is extended or adjusted under 35 U.S.C. 154(b) by 205 days.

(21) Appl. No.: 14/317,556

(22) Filed: Jun. 27, 2014

(65) Prior Publication Data

US 2015/0374318 A1    Dec. 31, 2015

(51) Int. Cl.
| | |
|---|---|
| A61B 6/00 | (2006.01) |
| A61B 5/055 | (2006.01) |
| A61B 6/03 | (2006.01) |
| A61B 5/00 | (2006.01) |
| G01R 33/48 | (2006.01) |

(52) U.S. Cl.
CPC .......... *A61B 6/4417* (2013.01); *A61B 5/0035* (2013.01); *A61B 5/055* (2013.01); *A61B 6/037* (2013.01); *A61B 6/5205* (2013.01); *A61B 6/5235* (2013.01); *G01R 33/481* (2013.01); *A61B 6/5258* (2013.01); *A61B 2576/00* (2013.01)

(58) Field of Classification Search
CPC ... A61B 6/037; A61B 17/00234; A61B 5/055; A61B 5/06; A61B 5/14532
See application file for complete search history.

(56) References Cited

U.S. PATENT DOCUMENTS

| | | | |
|---|---|---|---|
| 4,165,479 A | 8/1979 | Mansfield | |
| 4,307,343 A | 12/1981 | Likes | |
| 6,516,213 B1* | 2/2003 | Nevo | A61B 5/06 600/410 |
| 7,821,264 B2 | 10/2010 | Koch et al. | |
| 7,952,356 B2 | 5/2011 | Koch et al. | |
| 8,274,286 B2 | 9/2012 | Koch et al. | |
| 8,421,459 B2 | 4/2013 | Koch | |
| 2008/0146914 A1 | 7/2008 | Polzin et al. | |
| 2008/0319310 A1* | 12/2008 | Mukherjee | A61B 5/14532 600/420 |
| 2009/0185981 A1 | 7/2009 | Karczmar et al. | |
| 2012/0155733 A1* | 6/2012 | Wagenkenecht | G06T 7/0081 382/131 |
| 2014/0250676 A1* | 9/2014 | Lang | A61F 2/30756 29/592 |

(Continued)

OTHER PUBLICATIONS

Koch, et al., Z-Selective Multi-Spectral 3d Imaging: A MAVRIC-SEMAC Hybrid, Proc. Intl. Soc. Mag. Reson. Med. 18 (2010).

(Continued)

*Primary Examiner* — Baisakhi Roy
(74) *Attorney, Agent, or Firm* — Grogan, Tuccillo & Vanderleeden, LLP

(57) ABSTRACT

A method for attenuation correcting a PET image of a target includes locating a radiopaque structure by MRI scan of the target; fitting a model of the radiopaque structure to the MRI scan image; and correcting attenuation of the PET image based on the fitted model.

17 Claims, 7 Drawing Sheets

(56) References Cited

U.S. PATENT DOCUMENTS

2015/0110374 A1* 4/2015 Traughber ............ G01R 33/481
　　　　　　　　　　　　　　　　　　　　　　　　382/131

OTHER PUBLICATIONS

Koch, et al., An Automated Spectral Bin Construction Strategy to Enable T1 Contrast in MAVRIC SL, Proc. Intl. Soc. Mag. Reson. Med. (Apr. 2013).

* cited by examiner

METHOD, APPARATUS, AND ARTICLE FOR PET ATTENUATION CORRECTION UTILIZING MRI

BACKGROUND

Technical Field

Embodiments of the invention relate generally to medical diagnostic imaging. Particular embodiments relate to attenuation correction of positron emission tomography ("PET") images, using data concurrently obtained from magnetic resonance imaging ("MRI").

Discussion of Art

PET scanners use one or more rings of scintillators or other detectors to generate electrical signals from gamma rays (photon pairs) that are produced from the recombination of electrons, within a target material, e.g., human body tissue, and positrons, emitted from decay of a radionuclide packaged in a tracer compound. Typically, recombination events occur within about 1 mm from the radionuclide decay event, and the recombination photons are emitted in generally opposite directions to arrive at different detectors. Paired photon arrivals that occur within a detection window, usually less than a few nanoseconds apart, are counted as indicating a recombination event. On this basis, computed tomography algorithms are applied to the scintillator position and detection data in order to locate the various recombination events, thereby producing three-dimensional images of the tracer disposition within the target material.

Typically, the tracer compound is a liquid analogue to a biologic fluid and the radionuclide is disposed primarily in body tissues that make use of the biologic fluid. For example, a common form of PET makes use of fludeoxyglucose ($^{18}$F), which is analogous to glucose with the $^{18}$F radionuclide substituted for one of the glucose hydroxyl groups. Importantly, fludeoxyglucose is preferentially absorbed by brain matter, by the kidneys, and by growing cells, e.g., metastasizing cancer cells. As a result, PET is frequently used for oncologic studies, for localizing particular organs, and for studying metabolic processes.

One potential challenge in obtaining optimal PET image quality is that gamma rays, in the energy spectrum produced by positron-electron interactions, are easily attenuated by typical body tissues and are differently attenuated by different types of body tissue. As will be appreciated, varying attenuation can diminish statistical confidence in the locations of recombination events, thereby making the computed image "fuzzier" than is desirable. Accordingly, it is desirable to provide means for attenuation correction ("AC"). This is particularly desirable and challenging for patients who have highly radiopaque inclusions, such as cobalt-chromium joint replacements or nitinol stents.

Currently, computed tomography (CT) scanning is used concurrently with PET in order to obtain a model of tissue density that is suitably accurate for AC of the PET image. CT scanning utilizes x-rays to generate images. It is desirable, however, to provide a mode of PET attenuation correction that is not reliant on x-ray exposure.

BRIEF DESCRIPTION

In view of the above, aspects and embodiments of the invention provide attenuation correction of a PET image for a patient having radiopaque and paramagnetic implants or the like utilizing MRI.

In embodiments, a method is provided for attenuation correcting a PET image of a target. The method includes locating a radiopaque structure by MRI scan of the target; fitting a model of the radiopaque structure to the MRI scan image; and correcting attenuation of the PET image, based on the fitted model.

In other embodiments, the inventive method is implemented in an apparatus that includes a PET detector, a magnetic resonance magnet assembly, and a controller configured to operate the PET detector and the magnet assembly for locating a radiopaque structure by MRI scan of the target; fitting a model of the radiopaque structure to the MRI scan image; and correcting attenuation of the PET image, based on the fitted model.

In another embodiment, an article of computer-readable media is encoded with a PET image that is attenuation corrected according to a process that includes locating a radiopaque structure by MRI scan of the target and then fitting a model of the radiopaque structure to the MRI scan image. The process further includes correcting attenuation of the PET image, based on the fitted model.

DRAWINGS

The present invention will be better understood from reading the following description of non-limiting embodiments, with reference to the attached drawings, wherein below:

DETAILED DESCRIPTION

Figure 1:
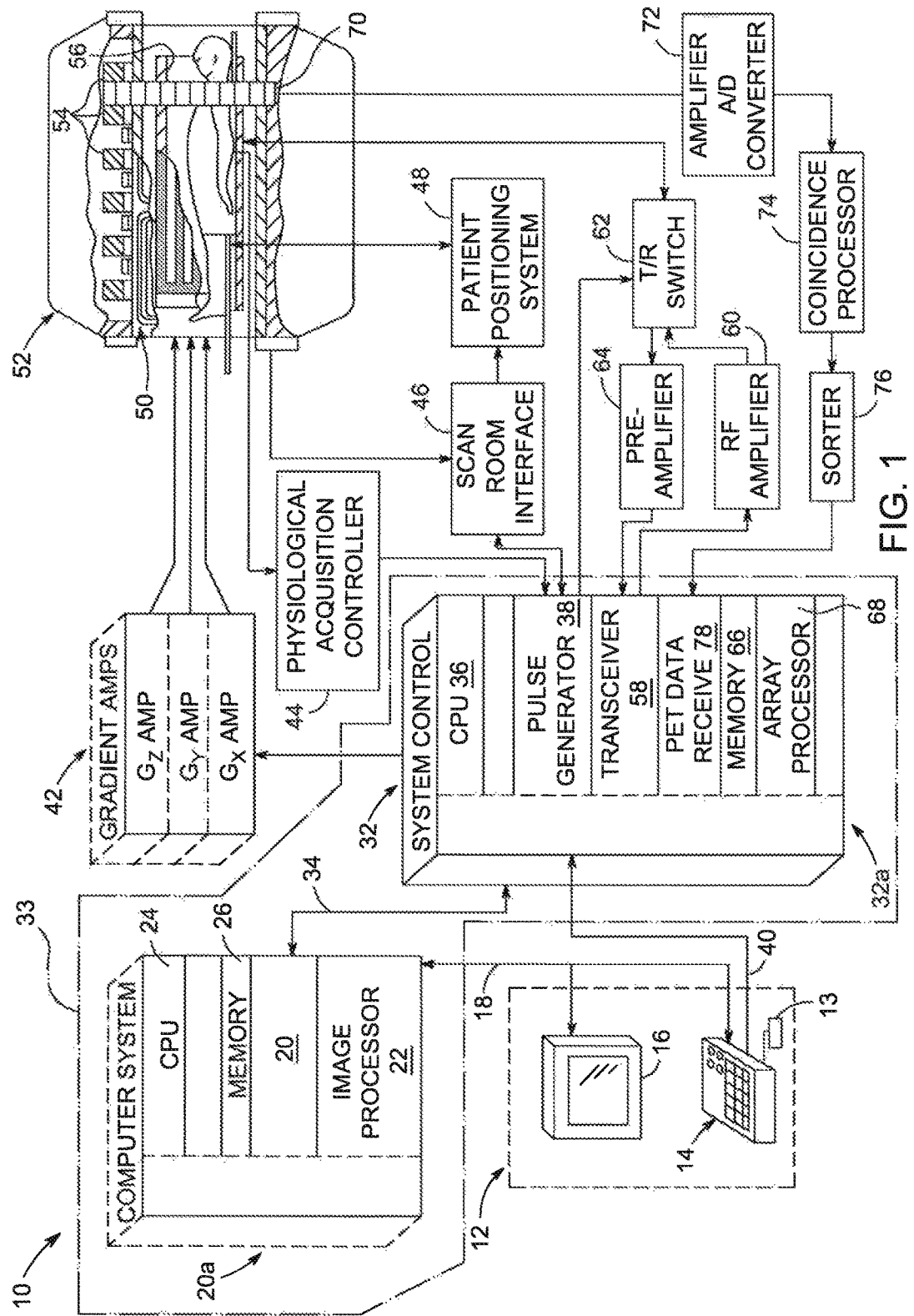
FIG. 1 illustrates schematically a magnetic resonance imaging system configured for use with an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description. Although aspects of the invention relate to attenuation correction for PET imaging, the invention more generally relates to estimation of paramagnetic structural shapes that are not directly perceptible from MRI.

Embodiments of the present invention are generally applicable to MRI, though exemplary embodiments are described with respect to multispectral 3D magnetic resonance imaging (MS 3D MRI). As will be appreciated, embodiments of the invention are not limited to human body tissue but may be used with other types of animal tissue.

FIG. 1 shows major components of an exemplary system 10 that combines MRI with PET and is configured for use with embodiments of the present invention. The system 10 includes an operator console 12, which is provided for control of the system 10. As part of the operator console 12, an input device 13 can include a mouse, joystick, keyboard, track ball, touch activated screen, light wand, voice control, or any similar or equivalent input device, and may be used for interactive geometry prescription. Additionally, the operator console 12 includes a control panel 14 as well as a display screen 16. The console 12 communicates through a link 18 with a separate computer system 20, which generates images for presentation to an operator via the display screen 16.

The computer system 20 includes a number of modules that communicate with each other through a backplane 20a. The modules of the computer system 20 include an image processor module 22, a CPU module 24 and a memory module 26 that may include a frame buffer for storing image data arrays. The computer system 20 communicates with a separate system control 32 through a high-speed signal link 34. The computer system 20 and the system control 32 collectively form an "MRI controller" 33. According to embodiments and aspects of the invention, the MRI controller 33 is configured to accomplish both MRI and PET, according to algorithms further discussed below.

The system control 32 includes a set of modules connected together by a backplane 32a. These include a CPU module 36 as well as a pulse generator module 38. The CPU module 36 connects to the operator console 12 through a serial link 40. It is through link 40 that the system control 32 receives commands from the operator to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to several components that are operated by the MRI controller 33, including the pulse generator module 38 (which controls a gradient amplifier 42, further discussed below), a physiological acquisition controller 44, and a scan room interface circuit 46. The CPU module 36 receives patient data from the physiological acquisition controller 44, which receives signals from a number of different sensors connected to the patient, such as ECG signals from electrodes attached to the patient and receives signals from various sensors associated with the condition of the patient and the magnet system from circuit 46. Moreover, the MRI controller 33 commands a patient positioning system 48 to move the patient or client C to a desired position for the scan via the interface circuit 46.

The pulse generator module 38 operates the gradient amplifiers 42 to achieve desired timing and shape of the gradient pulses that are produced during the scan. The gradient waveforms produced by the pulse generator module 38 are applied to the gradient amplifier system 42 having Gx, Gy, and Gz amplifiers. Each gradient amplifier excites a corresponding physical gradient coil in a gradient coil assembly, generally designated 50, to produce the magnetic field gradients used for spatially encoding acquired signals. The gradient coil assembly 50 forms part of a magnet assembly 52, which also includes a polarizing magnet 54 and a whole-body RF coil 56. In an embodiment of the invention, RF coil 56 is a multi-channel coil.

A transceiver module 58 in the system control 32 produces pulses that are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 32 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either transmit mode or receive mode.

After the multi-channel RF coil 56 picks up the RF signals produced from excitation of the target, the transceiver module 58 digitizes these signals. The MRI controller 33 then processes the digitized signals by Fourier transform to produce k-space data, which then is transferred to a memory module 66, or other computer readable media, via the system control 32. "Computer readable media" may include, for example, structures configured so that electrical, optical, or magnetic states may be fixed in a manner perceptible and reproducible by a conventional computer: e.g., text or images printed to paper or displayed on a screen, optical discs, or other optical storage media; "flash" memory, EEPROM, SDRAM, or other electrical storage media; floppy or other magnetic discs, magnetic tape, or other magnetic storage media. A scan is complete when an array of raw k-space data has been acquired in the computer readable media 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

Figure 2:
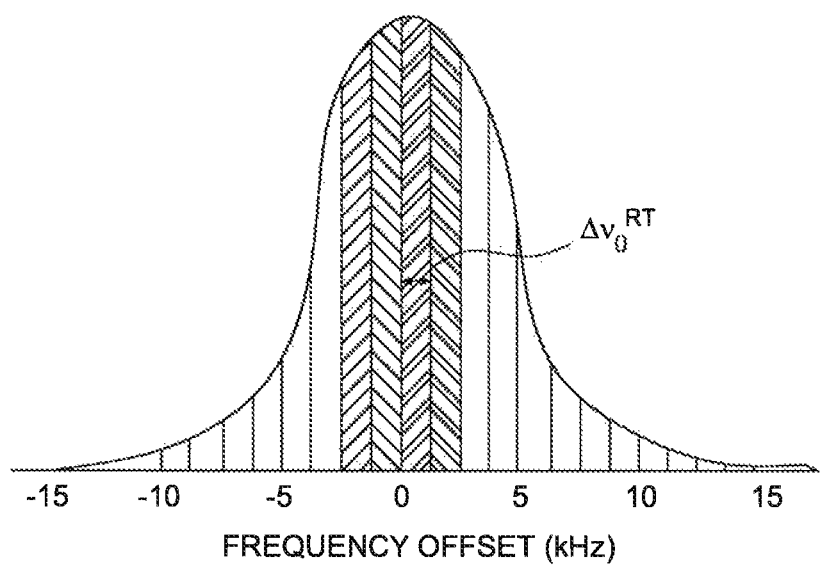
FIG. 2 depicts frequency offsets resultant from MRI of a target with a paramagnetic inclusion.

When scanning a target, client C, who has a paramagnetic inclusion or implant, e.g., a bone screw or joint replacement, the implant distorts both the static field B0 and the gradient waveforms Gx, Gy, Gz in such a way that the frequency response at any given point within the target may be offset from an expected "zero" frequency, as shown in FIG. 2. For example depending on proximity to an implant, a particular location within the target may respond anywhere between about 15 kHz below or above the expected frequency response. Because localization of image pixels depends on correlating frequency responses, the frequency offsets caused by paramagnetic inclusion result in distorted images with pixels displaced from where they should be shown. 3-D multispectral MRI is known to resolve issues with frequency offsets, by superimposing images obtained contemporaneously from plural frequencies.

Referring again to FIG. 1, the combined PET-MRI system 10 also contains a positron emission detector 70. The detector 70 may be of any suitable construction for acquiring PET data. In an embodiment, the detector 70 is configured to detect gamma rays from positron annihilations emitted from a subject and includes a plurality of scintillators and photodetectors arranged about a gantry. The scintillator components, photodetectors, and other electronics of the detector 70 need not be shielded from the magnetic fields and/or RF fields applied by the MR components 54, 56. It is contemplated, however, that embodiments of the present invention may include such shielding as known in the art, or may be combined with various shielding techniques.

Gamma ray incidences detected by detector 70 are transformed, by the photodetectors of the detector 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. As a result, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 66 for subsequent processing by processor 68. PET images may then be reconstructed by image processor 22 and may be combined with MR images to produce hybrid structural and metabolic or functional images. Conditioning circuits 72, coincidence processor 74 and sorter 76 may each be external of the controller 33, or may be integrated therein as shown in FIG. 1.

As discussed above, presence of a paramagnetic inclusion will detract from MRI. Similarly, presence of a radiopaque structure will detract from PET. Many, but not all, radiopaque materials are also paramagnetic. Fortunately, all radiopaque materials commonly used for medical implants are paramagnetic. As a result, it is generally possible to utilize MRI anomalies both for detecting radiopaque inclusions and for correcting PET attenuation errors produced by those inclusions, according to the inventive methods discussed below.

Figure 3:
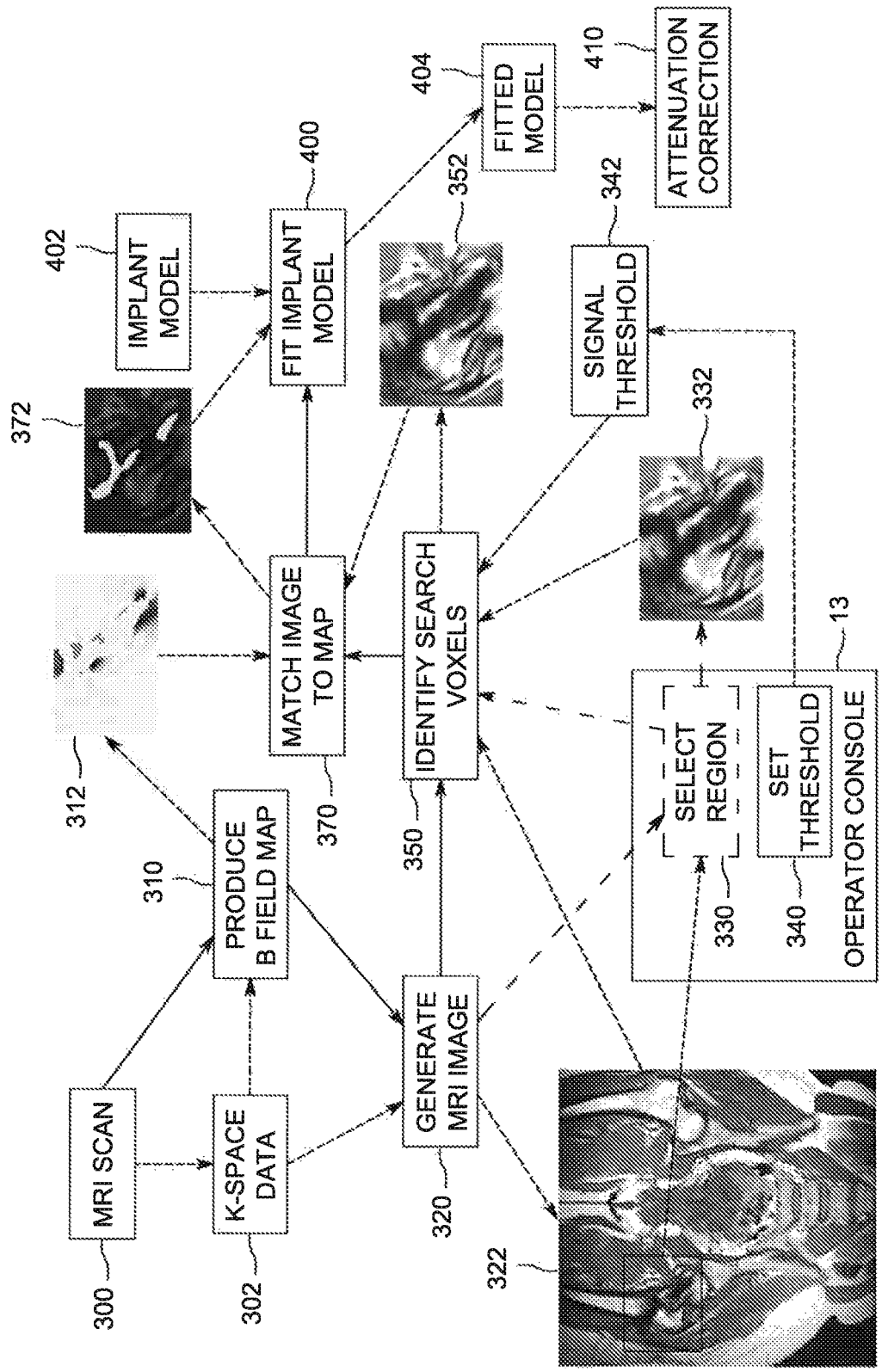
FIG. 3 illustrates schematically an overview of a method for utilizing MRI to obtain PET attenuation correction, according to an embodiment of the invention.

FIG. 3 illustrates an exemplary embodiment of the invention, in which the combined PET/MRI system 10 performs an MRI scan 300, according to a multispectral 3D protocol, and also performs a PET scan. The MRI scan 300 and the PET scan may be performed concurrently (by simultaneous operation of the detector 70 and the magnet assembly 52), or contemporaneously (alternate operation of the detector 70 and the magnet assembly 52, during a single procedure). From the MRI scan 300 the controller 33 obtains k-space data 302, and produces 310 a 3D magnetic field map 312 based on all or a subset of the k-space data. For example, by utilizing a 3 Tesla polarizing field, a magnetic field map 312 with 1 cm to 2 cm 3D resolution can be acquired from central k-space in about 2 minutes. From the PET scan the controller 33 obtains scintillation data. Because a radiopaque structure may occlude some photons that would otherwise be detected, the PET scan scintillation data requires attenuation correction in order to produce a fully usable image. Attenuation correction, in turn, requires an accurate estimate of the radiopaque structure location and position.

In order to estimate location and position of a radiopaque structure, the MRI controller 33 searches the k-space data 302 for an anomaly consistent with a radiopaque structure. For example, the MRI controller 33 generates 320 from the k-space data 302 a 3D MRI image 322. For processing efficiency, the MRI controller 33 may select 330 only a portion of the MRI image 322 that encompasses a known implant region 332. For example, an operator may use the console 13 to select 330 the known implant region 332. The MRI controller 33 also sets 340 a signal threshold 342, and within the MRI image 322, identifies 350 search voxels 352 that meet the signal threshold 342. In place of having an operator select a known implant region, or as a preliminary thereto, the MRI controller 33 may use image landmarks or density of search voxels 352 to identify one or more potential implant regions 332 within the MRI image 322. Also, although FIG. 3 shows setting 340 the signal threshold 342 via the input device 13, equally, the MRI controller 33 may set the signal threshold 342 based on statistical analysis of the voxels within the MRI image 322 or the selected region 332.

Next, the MRI image 322, or at least the known implant region 332, is matched 370 to the magnetic field map 312 or to a corresponding portion thereof, in order to form a composite image 372. For example, for each search voxel 352, a unit dipolar field is constructed. A cost function then is computed within F comparing the generated field to the voxels of the magnetic field map 312, where COST=SUM(‖λ*DipoleField(F)−FieldMap(F)‖)

The cost function for each search voxel 352 is calculated for differing dipole moments, X, which are determined by pre-determined search criteria for a given implant. Each search voxel 352 then is assigned the dipole moment that results in the lowest cost function value.

Within the composite image 372, the search voxels 352 are used as source points for "fitting" 400 an implant model 402 to the field map 312. Fitting 400 may be accomplished according via algorithm including, but not limited to any of several exemplary algorithms further discussed below. The fitted implant model 404 then is pushed through the MRI controller 33 to a PET attenuation correction ("AC") algorithm 410, which calculates how the modeled implant would attenuate detection of photons emitted toward each of the detectors 70 from the known positron annihilation positions 332.

Figure 4:
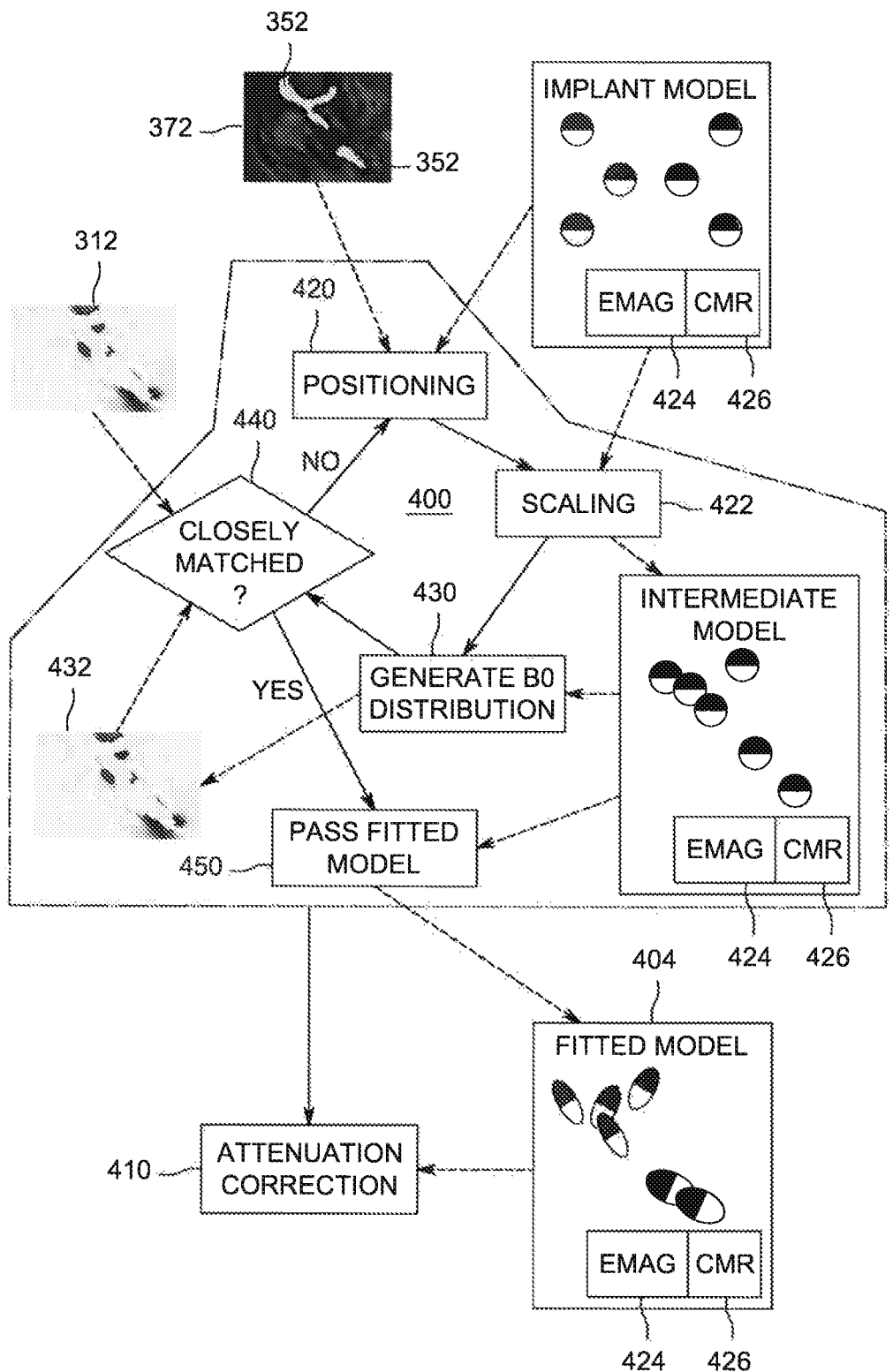
FIG. 4 illustrates schematically a method for fitting an implant model to a magnetic field map, in order to estimate photon attenuation by the implant model, according to an embodiment of the invention.

In an embodiment of the invention shown in FIG. 4, the implant model 402 includes a small plurality (2-7) of balls or spheres 412, which are modeled as superimposed dipolar field sources. The MRI system 10 fits 400 the implant structure model 402 to the field map 312 by iteratively positioning 420 and scaling 422 each of the spheres 412 to obtain intermediate models 425 from which the MRI controller 33 generates 430 B0 distributions 432. For each intermediate model 425, the MRI controller 33 assesses whether the generated B0 distribution 432 closely matches 440 the magnetic field map 312. Close matching between the B0 distribution 432 and the field map 312, may mean a match that provides a local minimum of an Euler distance between the corresponding field vector matrices; or a match that provides a local minimum of a cost function as discussed above regarding the matching of the MRI image to the magnetic field map. Other matching heuristics will be apparent to skilled workers in light of this disclosure.

As used herein, "positioning" 420 may begin by locating the spheres at centroids of groupings of the search voxels 352 within the composite image 372, and also may include varying orientation, relative positions, and spacing among the spheres. "Scaling" 422 includes varying the size of the spheres, and also may include iteration through known combinations of material electromagnetic properties 424, such as, e.g., magnetic permittivity and permeability, along with associated chemical, mechanical, and radiologic ("CMR") properties 426 such as, e.g., density and radiopacity. Once the spheres 412 have been optimally fitted, then the fitted model 404 can be passed 450 to the AC algorithm 410, which models photon attenuation by the fitted model 404.

Figure 5:
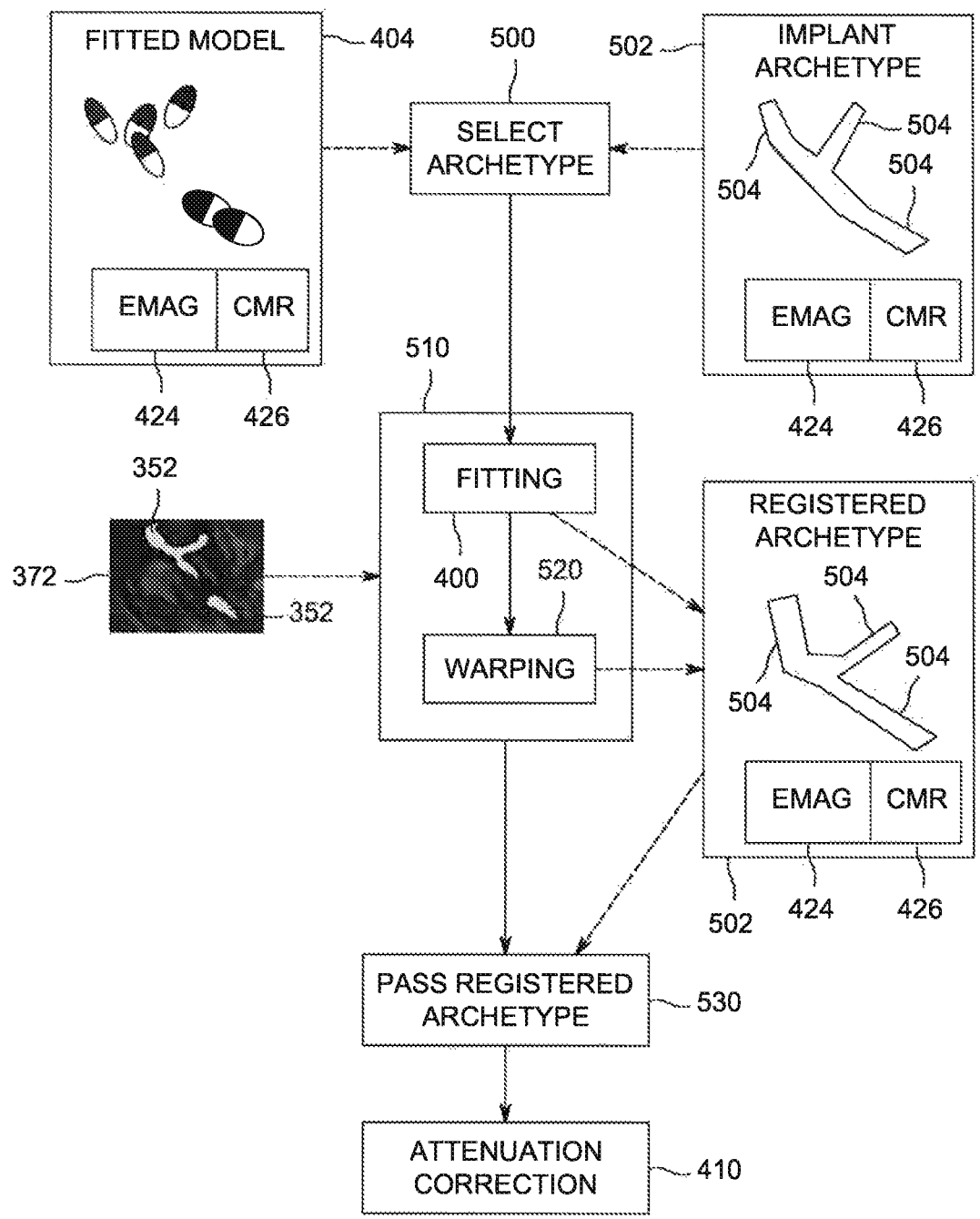
FIG. 5 illustrates schematically a method for fitting an implant archetype to a magnetic field map, in order to estimate photon attenuation by the implant archetype, according to an embodiment of the invention.

In another embodiment of the invention, shown in FIG. 5, a similar finite dipole modeling concept is used. Here, instead of passing the fitted model 404 immediately into the AC algorithm 410, the fitted model 404 instead is used to select 500 one of several implant archetypes 502. More particularly, the fitted model 404 is correlated to structural features 504 and material parameters 424, 426 of known potential field disturbance sources (i.e. total hip replacement, total knee replacement, fixation screws, spinal fusion devices, etc.; collectively, "archetypes"), and the archetype 502 having the closest correlation is selected. Each of the implant archetypes 502 may be as simple as a ball-and-stick representation, but with pre-defined dimension 504 and material properties 424, 426. In certain embodiments, some or all of the implant archetypes 502 are significantly more detailed than the fitted model 404, for example, they may include solid models of actual implant products with specified material properties, as further discussed below with reference to FIG. 6.

Once an implant archetype has been selected 500, the archetype 502 then is registered 510 to the composite image 372, generally according to the steps of fitting 400 as discussed above with reference to FIG. 4. However, given that the archetype 502 has a more detailed shape and installation location, an additional warping transform 520 may be trialed for any portions of the archetype expected to sustain torsion or bending moments as installed. The registered archetype 522 then is passed 530 to the AC algorithm 410.

Figure 6:
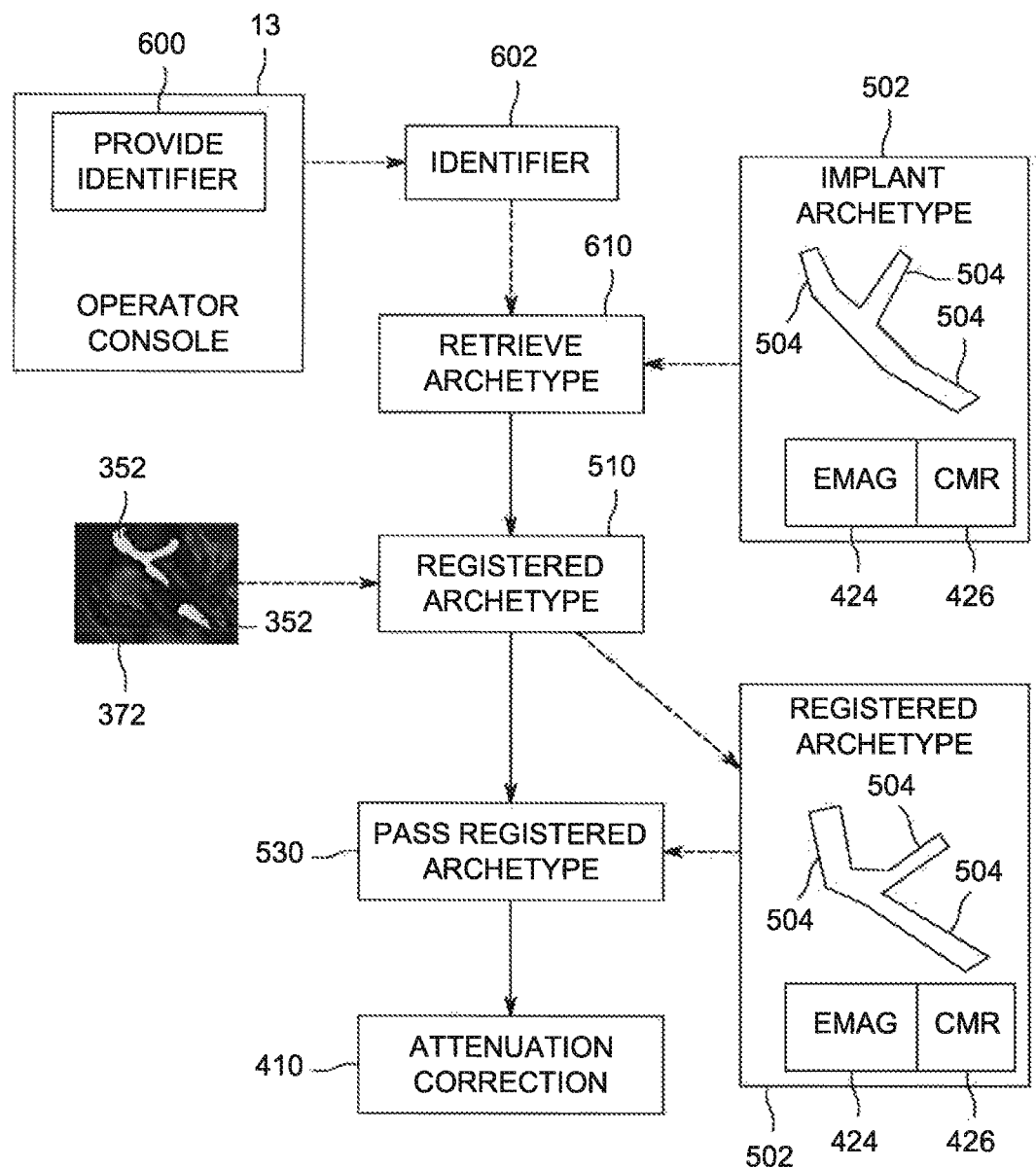
FIG. 6 illustrates schematically a method for retrieving an implant archetype from a catalog, based on an implant identifier, according to an embodiment of the invention.

In yet another embodiment of the invention, shown in FIG. 6, the MRI controller 33 may be provided 600 with an identifier 602 of a client's implant via the input device 13. The identifier may be a model number. In certain embodiments, the identifier 602 may be a unit product inventory code. Based on the identifier 602, the MRI controller 33 can retrieve 610 from a catalog 612 an archetype 502 of the implant as it was designed (for a model number identifier) or as it was installed (for a unit product inventory code). Then the archetype 502 may be registered 510, generally as discussed above with reference to the archetypes 502. In this embodiment, however, the registration 510 may be tuned to focus on positioning 420 and warping 520, since material properties may be presumed to match the catalog 612. As the archetype 502 may be presumed closely accurate to the inclusion actually present in the patient, it may be worthwhile to obtain a field map 312 with greater resolution, i.e. with voxels of less than 1 cm.

Figure 7:
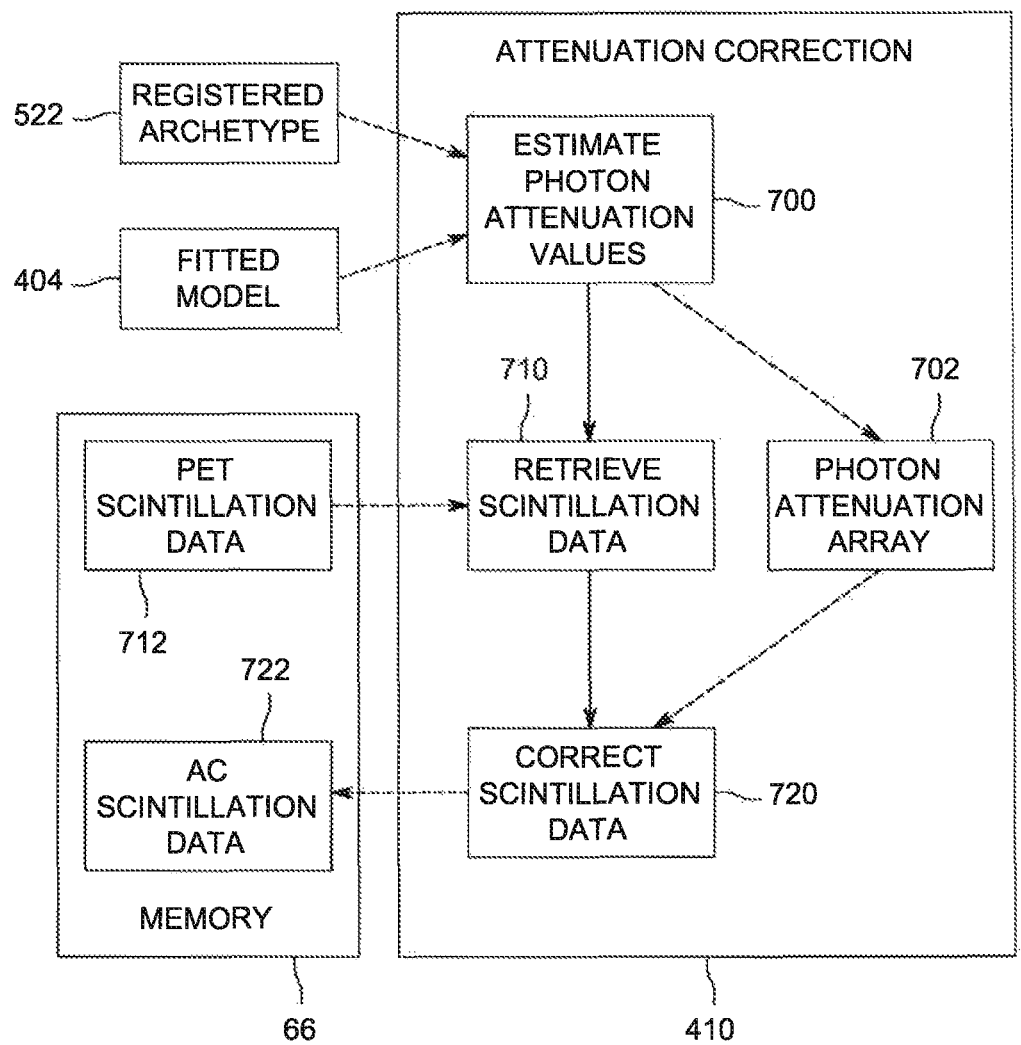
FIG. 7 illustrates a process for attenuation correction of a PET image, according to an embodiment of the invention.

Referring now to FIG. 7, the attenuation correction algorithm 410 receives the fitted model 404, or the registered archetype 522, and, from that basis, corrects attenuation of the PET image. In particular, as part of correcting attenuation, the attenuation correction algorithm 410 estimates 700 an array 702 of photon attenuation values, according to conventional methods. The attenuation correction algorithm 410 then retrieves 710 scintillation data 712 from the memory 66, corrects 720 the scintillation data according to the photon attenuation values array 702, and records the attenuation corrected scintillation data 722 back into the memory 66. Thus, correcting attenuation, according to some aspects of the invention, includes utilizing MRI data to initialize a computation of photon attenuation values, as well as refining scintillation data according to the computed values of photon attenuation.

In embodiments, a method is provided for attenuation correcting a PET image of a target. The method includes locating a radiopaque structure by MRI scan of the target; fitting a model of the radiopaque structure to the MRI scan image; and correcting attenuation of the PET image, based on the fitted model. Locating the radiopaque structure may include mapping a magnetic field from MR data, and identifying in the magnetic field map an anomaly consistent with the radiopaque structure. Fitting a model may include identifying search voxels within a 3-D MRI image, and forming a composite image by matching the magnetic field map to the 3-D MRI image. Identifying search voxels may include setting a signal threshold for selecting search voxels. Matching the magnetic field map to the 3-D MRI image may include computing, for each search voxel of the MRI image, a generated field and a cost function comparison of the generated field to the magnetic field map. Fitting a model may include scaling and positioning a plurality of superimposed dipole field sources to obtain a fitted model that generates a B0 distribution closely matching the magnetic field map, e.g., obtaining a local minimum of a point-by-point cost function between the generated B0 distribution and the magnetic field map. Fitting a model may further include selecting an implant archetype that has structural features and material parameters correlated with the fitted model; and scaling, positioning, and warping the implant archetype to obtain a local minimum of a point-by-point cost function. Also, fitting a model may include obtaining an identifier of a client's implant, retrieving from a catalog a detailed solid model matching the identifier, and scaling, positioning, and warping the detailed solid model to obtain a fitted model that generates a B0 distribution at a local minimum of a point-by-point cost function from the magnetic field map.

In certain embodiments, the inventive method is implemented in an apparatus that includes a PET detector, a magnetic resonance magnet assembly, and a controller configured to operate the PET detector and the magnet assembly for locating a radiopaque structure by MRI scan of the target; fitting a model of the radiopaque structure to the MRI scan image; and correcting attenuation of the PET image, based on the fitted model.

In other embodiments, an article of computer-readable media is encoded with a PET image that is attenuation corrected according to a process that includes locating a radiopaque structure by MRI scan of the target and then fitting a model of the radiopaque structure to the MRI scan image. The process further includes correcting attenuation of the PET image based on the fitted model.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and apparatus, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for attenuation correcting a PET image of a target, comprising:
   locating a radiopaque structure by MRI scan of the target;
   fitting a model of the radiopaque structure to the MRI scan image;
   correcting attenuation of the PET image based on the fitted model; and
   wherein
   locating the radiopaque structure includes mapping a magnetic field from MR data, and identifying in the magnetic field map an anomaly consistent with the radiopaque structure, and
   fitting a model includes identifying search voxels within a 3-D MRI image and forming a composite image by matching the magnetic field map to the 3-D MRI image.

2. The method as claimed in claim 1, wherein identifying search voxels includes setting a signal threshold for selecting search voxels.

3. The method as claimed in claim 2, wherein matching the magnetic field map to the 3-D MRI image includes computing, for each search voxel of the MRI image, a generated field and a cost function comparison of the generated field to the magnetic field map.

4. The method as claimed in claim 1, wherein fitting a model includes scaling and positioning a plurality of superimposed dipole field sources to obtain a fitted model that generates a B0 distribution closely matching the magnetic field map.

5. The method as claimed in claim 4, wherein closely matching the magnetic field map includes obtaining a local minimum of a point-by-point cost function between the generated B0 distribution and the magnetic field map.

6. The method as claimed in claim 4, wherein fitting a model further includes selecting an implant archetype that has structural features and material parameters correlated with the fitted model.

7. The method as claimed in claim 6, wherein fitting a model further includes scaling, positioning, and warping the implant archetype to obtain a local minimum of a point-by-point cost function.

8. An apparatus for obtaining attenuation-corrected PET images of a target, said apparatus comprising:
   a PET detector;
   a magnetic resonance magnet assembly;
      a controller configured to operate the PET detector and the magnet assembly for locating a radiopaque structure by MRI scan of the target, fitting a model of the radiopaque structure to the MRI scan image, and correcting attenuation of the PET image based on the fitted model; and
   wherein
      locating the radiopaque structure includes mapping a magnetic field from MR data, and identifying in the magnetic field map an anomaly consistent with the radiopaque structure, and
      fitting a model includes identifying search voxels within a 3-D MRI image and forming a composite image by matching the magnetic field map to the 3-D MRI image.

9. The method as claimed in claim 1, wherein fitting a model includes obtaining an identifier of a client's implant, retrieving from a catalog an implant archetype matching the identifier, and scaling, positioning, and registering the implant archetype.

10. The apparatus as claimed in claim 8, wherein identifying search voxels includes setting a signal threshold for selecting search voxels.

11. The apparatus as claimed in claim 10, wherein matching the magnetic field map to the 3-D MRI image includes computing, for each search voxel of the MRI image, a generated field and a cost function comparison of the generated field to the magnetic field map.

12. The apparatus as claimed in claim 8, wherein fitting a model includes scaling and positioning a plurality of superimposed dipole field sources to obtain a fitted model that generates a B0 distribution closely matching the magnetic field map.

13. The apparatus as claimed in claim 12, wherein closely matching the magnetic field map includes obtaining a local minimum of a point-by-point cost function between the generated B0 distribution and the magnetic field map.

14. The apparatus as claimed in claim 12, wherein fitting a model further includes selecting an implant archetype that has structural features and material parameters correlated with the fitted model.

15. The apparatus as claimed in claim 14, wherein fitting a model further includes scaling, positioning, and warping the implant archetype to obtain a local minimum of a point-by-point cost function.

16. The apparatus as claimed in claim 8, wherein fitting a model includes obtaining an identifier of a client's implant, retrieving from a catalog an implant archetype matching the identifier, and scaling, positioning, and registering the implant archetype.

17. A non-transitory computer-readable media encoded with a PET image that is attenuation corrected according to a process comprising:
  locating a radiopaque structure by MRI scan of the target;
  fitting a model of the radiopaque structure to the MRI scan image;
  correcting attenuation of the PET image based on the fitted model; and
  wherein
    locating the radiopaque structure includes mapping a magnetic field from k-space obtained from the MRI scan of the target, and identifying in the magnetic field map an anomaly consistent with the radiopaque structure, and
    fitting a model includes identifying search voxels within a 3-D MRI image and forming a composite image by matching the magnetic field map to the 3-D MRI image.

* * * * *